US008981059B2

(12) United States Patent
Umeda et al.

(10) Patent No.: US 8,981,059 B2
(45) Date of Patent: Mar. 17, 2015

(54) PLATELET AGGREGATION INDUCING SUBSTANCE

(71) Applicant: JNC Corporation, Tokyo (JP)

(72) Inventors: Yasuto Umeda, Kumamoto (JP);
Shinichi Takasaki, Kanagawa (JP);
Takafumi Takebayashi, Kanagawa (JP);
Takahiro Kawai, Kumamoto (JP)

(73) Assignee: JNC Corporation, Tokyo (JP)

( * ) Notice: Subject to any disclaimer, the term of this patent is extended or adjusted under 35 U.S.C. 154(b) by 0 days.

(21) Appl. No.: 14/180,355

(22) Filed: Feb. 14, 2014

(65) Prior Publication Data
US 2014/0287233 A1 Sep. 25, 2014

Related U.S. Application Data

(62) Division of application No. 12/520,508, filed as application No. PCT/JP2007/073910 on Dec. 12, 2007, now Pat. No. 8,686,117.

(30) Foreign Application Priority Data

Dec. 21, 2006 (JP) .................................. 2006-344553
Apr. 26, 2007 (JP) .................................. 2007-116349

(51) Int. Cl.
A61K 35/14 (2006.01)
A61K 38/17 (2006.01)
C07K 14/00 (2006.01)
C07K 14/78 (2006.01)

(52) U.S. Cl.
CPC ............... C07K 14/001 (2013.01); C07K 14/78 (2013.01)
USPC ......................................... 530/381; 530/356

(58) Field of Classification Search
None
See application file for complete search history.

(56) References Cited

U.S. PATENT DOCUMENTS

2003/0162941 A1  8/2003  Tanihara et al.

FOREIGN PATENT DOCUMENTS

| JP | 2002-537270 | 11/2002 |
|----|-------------|---------|
| JP | 2004-350677 | 12/2004 |
| JP | 2005-053878 | 3/2005  |
| JP | 2005-058499 | 3/2005  |
| JP | 2005-060314 | 3/2005  |
| JP | 2005-060315 | 3/2005  |
| JP | 2005-060550 | 3/2005  |
| JP | 2005-126360 | 5/2005  |
| JP | 2005-206542 | 8/2005  |
| WO | 0048625     | 8/2000  |

OTHER PUBLICATIONS

Rao et al., "Promition of Human Platelet Adhesion and Aggregation by a Synthetic, Triple-helical "Mini-collagen"", The Journal of Biological Chemistry, May 13, 1994, pp. 13899~13903, vol. 269, No. 19.
Morton et al., "Integrin α2β1-independent activation of platelets by simple collagen-like peptides: collagen tertiary (triple-helical) and quaternary (polymeric) structures are sufficient alone for α2β1-independent platelet reactivity", Biochem. J., 1995, pp. 337~344, vol. 306.
Knight et al., "Collagen-platelet interaction: Gly-Pro-Hyp is uniquely specific for platelet Gp VI and mediates platelet activation by collagen", Cardiovascular Research, 1999, pp. 450~457, vol. 41.
Detar et al., "Synthesis of Sequence Peptide Polymers Related to Collagen", The Journal of Organic Chemistry, 1972, pp. 4377~4380, vol. 37, No. 26.
Inoue et al., "Novel synthetic collagen fibers, poly(PHG), stimulate platelet aggregation through glycoprotein VI", FEBS Letters, 2009, pp. 81~87, vol. 583.
Kishimoto et al., "Synthesis of Poly(Pro-Hyp-Gly)n by Direct Polycondensation of (Pro-Hyp-Gly)n, Where n=1, 5, and 10, and Stability of the Triple-Helical Structure", Biopolymers, 2005, pp. 163~172, vol. 79.
Definition of "Hemostasis" from Medical Dictionary < http://medical-dictionary.thefreedictionary.com/hemostasis >—Downloaded Aug. 29, 2012.
Gan et al., "Effect of Increasing Doses of Aspirin on Platelet Aggregation among Stroke Patients", Cerebrovascular Diseases, 2002, pp. 252~255, vol. 14.
Machine Translation of JP2005-126360—original publication May 19, 2005.
Machine Translation of JP2005-058499—original publication Mar. 10, 2005.

Primary Examiner — Suzanne M Noakes
(74) Attorney, Agent, or Firm — Jianq Chyun IP Office

(57) ABSTRACT

A platelet aggregation inducing substance containing as an active ingredient a polypeptide having a peptide fragment represented by formula (1) (component A):

$$-(\text{Pro-X-Gly})_n- \qquad (1)$$

wherein X represents Pro or Hyp; and n represents an integer of from 20 to 5,000.

9 Claims, 9 Drawing Sheets

PLATELET AGGREGATION INDUCING SUBSTANCE

CROSS-REFERENCE TO RELATED APPLICATION

This application is a divisional application and claims priority benefits of patent application Ser. No. 12/520,508, filed on Jun. 19, 2009, now allowed, which is a 371 application of an International PCT Application serial no. PCT/JP2007/073910, filed on Dec. 12, 2007, which claims priority benefits of Japan Patent Application No. 2006-344553 filed on Dec. 21, 2006 and Japan Patent Application No. 2007-116349 filed on Apr. 26, 2007. The entirety of each of the above-mentioned patent applications, and the computer readable form (CRF) copy of the "Sequence Listing" already filed on Jan. 31, 2012 for patent application Ser. No. 12/520,508 are hereby incorporated by reference herein and made a part of this specification. The CRF copy of the sequence listing for this application is identical to the CRF copy of "Sequence Listing" filed for patent application Ser. No. 12/520,508.

TECHNICAL FIELD

The present invention relates to a platelet aggregation inducing substance that is capable of being used for evaluation of function of platelets.

BACKGROUND ART

Platelets are a biosubstance that is essential for hemostatic action upon bleeding, and in the case where the function thereof is exhibited excessively, thrombus is formed to cause critical diseases, such as myocardial infarction, cerebral infarction and the like. In the case where platelets fail to function, on the contrary, bleeding tendency is induced. Accordingly, for performing health management and medical treatment, it is important to comprehend the state of platelets in blood by evaluating the function thereof (measurement of aggregation capacity of platelets).

The aggregation capacity of platelets is generally measured in such a manner that aggregation of platelets is induced by adding an aggregation inducing substance, such as collagen and the like, to platelet-rich plasma under a low shear rate, and the transmittance increased by the aggregation is measured.

Collagen of animal origin is generally used for measuring aggregation capacity of platelets, and there are known ones that induce aggregation of platelets in artificially synthesized collagen.

Non-patent Document 1, 2 and 3 disclose a polypeptide -(Gly-Pro-Hyp)$_{10}$- having a triple helix structure and a substance obtained by crosslinking the polypeptide to form a quaternary structure, and also disclose the platelet aggregation inducing activity of the substances.

The polypeptide -(Gly-Pro-Hyp)$_{10}$- disclosed in the non-patent documents has low platelet aggregation inducing activity and cannot be used for measuring aggregation capacity of platelets.

The substance obtained by crosslinking the polypeptide to form a quaternary structure has higher platelet aggregation inducing activity as compared to the polypeptide and can be used for measuring aggregation capacity of platelets. For obtaining the substance, however, it is necessary to perform peptide synthesis reaction including repeated deprotection and formation of amino acid bond, and it is also necessary to perform crosslinking. Repetition of the reactions decreases the yield of the target reaction product. The decrease in yield results in increase of cost.

[Non-patent Document 1] THE JOURNAL OF BIOLOGICAL CHEMISTRY, May 13, 1994, 269(19), 13899-18903
[Non-patent Document 2] The Biochemical Journal, 1995, 306, 337-344
[Non-patent Document 3] Cardiovascular Research, 1999, 41, 450-457

DISCLOSURE OF THE INVENTION

It is considered that artificially synthesized collagen is advantageous in such points as reproducibility, stability, preservability and the like, as compared to collagen of animal origin, which has been used as a substance for inducing aggregation of platelets. However, the synthetic collagen disclosed in Non-patent Documents 1, 2 and 3 involves such problems as low yield, high cost and the like. Furthermore, it involves failure in providing sufficient platelet aggregation inducing activity depending on the structure thereof.

There are cases where aspirin is used for preventing formation of thrombus, and aspirin in blood impairs the function of the platelet aggregation inducing substance, such as collagen or the like, thereby making considerably difficult the measurement of platelet aggregation capacity of a patient taking aspirin. Evaluation of function of platelets (measurement of aggregation capacity of platelets) is essential for performing health management and medical treatment as noted above, and thus such a substance is being demanded that effectively induces aggregation of platelets even in the presence of aspirin.

The inventors have made earnest investigations in view of the aforementioned problems associated with the conventional techniques. Consequently, it has been found that a polypeptide represented by formula (1) used in the invention can be obtained by polymerizing a trimer of -(Pro-Hyp-Gly)- in a solvent, thereby minimizing the reaction process, which is advantageous in yield and cost, has platelet aggregation inducing activity at such a level that can be sufficiently used for measurement of aggregation capacity of platelets, and is capable of effectively inducing aggregation of platelets even in the presence of aspirin, and thus the invention has been completed.

The invention includes the following aspects (1) to (8).

(1) A platelet aggregation inducing substance containing as an active ingredient a polypeptide having a peptide fragment represented by formula (1) (component A):

$$-(Pro-X-Gly)_n- \quad (1)$$

wherein X represents Pro or Hyp; and n represents an integer of from 20 to 5,000.

(2) The platelet aggregation inducing substance according to the item (1), wherein the peptide fragment (component A) contains a peptide unit represented by formula (2) (component B) and a peptide unit represented by formula (3) (component C), and a ratio of the component B and the component C (component B/component C, molar ratio) is in a range of from 95/5 to 0/100:

$$-(Pro-Pro-Gly)- \quad (2)$$

$$-(Pro-Hyp-Gly)- \quad (3)$$

(3) The platelet aggregation inducing substance according to the item (1) or (2), wherein the polypeptide further contains at least one selected from a peptide unit represented by formula (4), a peptide unit represented by formula (5), and a peptide fragment containing at least one of the peptide units (component D):

$$-(Y_1-Y_2-Gly)- \quad (4)$$

$$-(Pro-Z_1-Gly-Z_2-Ala-Gly)- \text{ (SEQ ID NO:13)} \quad (5)$$

wherein $Y_1$ represents Asp or Glu, which may have a carboxyl group at the γ-position; $Y_2$ represents Pro or Hyp; $Z_1$ represents Gln, Asn, Leu, Ile, Val or Ala; and $Z_2$ represents Ile or Leu. The peptide unit represented by formula (5) is selected from the group consisting of SEQ ID NO:1, SEQ ID NO:2, SEQ ID NO:3, SEQ ID NO: 4, SEQ ID NO: 5, SEQ ID NO: 6, SEQ ID NO: 7, SEQ ID NO: 8, SEQ ID NO:9, SEQ ID NO:10, SEQ ID NO:11 and SEQ ID NO:12.

(4) The platelet aggregation inducing substance according to the item (3), wherein a ratio of the peptide fragment (component A) and at least one selected from the peptide unit represented by formula (4), the peptide unit represented by formula (5), and the peptide fragment containing at least one of the peptide units (component D) (component A/component D, molar ratio) is in a range of from 99/1 to 30/70.

(5) The platelet aggregation inducing substance according to one of the items (1) to (4), wherein the polypeptide exhibits positive Cotton effect at a wavelength of from 220 to 230 nm and negative Cotton effect at a wavelength of from 195 to 205 nm in a circular dichroic spectrum.

(6) The platelet aggregation inducing substance according to one of the items (1) to (5), wherein the polypeptide has a molecular weight in a range of from 10,000 to 500,000,000.

(7) The platelet aggregation inducing substance according to one of the items (1) to (6), wherein the polypeptide has a particle diameter in a range of from 0.01 to 1,000 μm.

(8) The platelet aggregation inducing substance according to one of the items (1) to (7), wherein the polypeptide has a viscosity in a range of from 10 to 10,000 mPa·s, wherein the viscosity is measured for a 1 wt % aqueous solution of the polypeptide under a condition of 20° C. with an E-type viscometer.

BEST MODE FOR CARRYING OUT THE INVENTION

Figure 1:
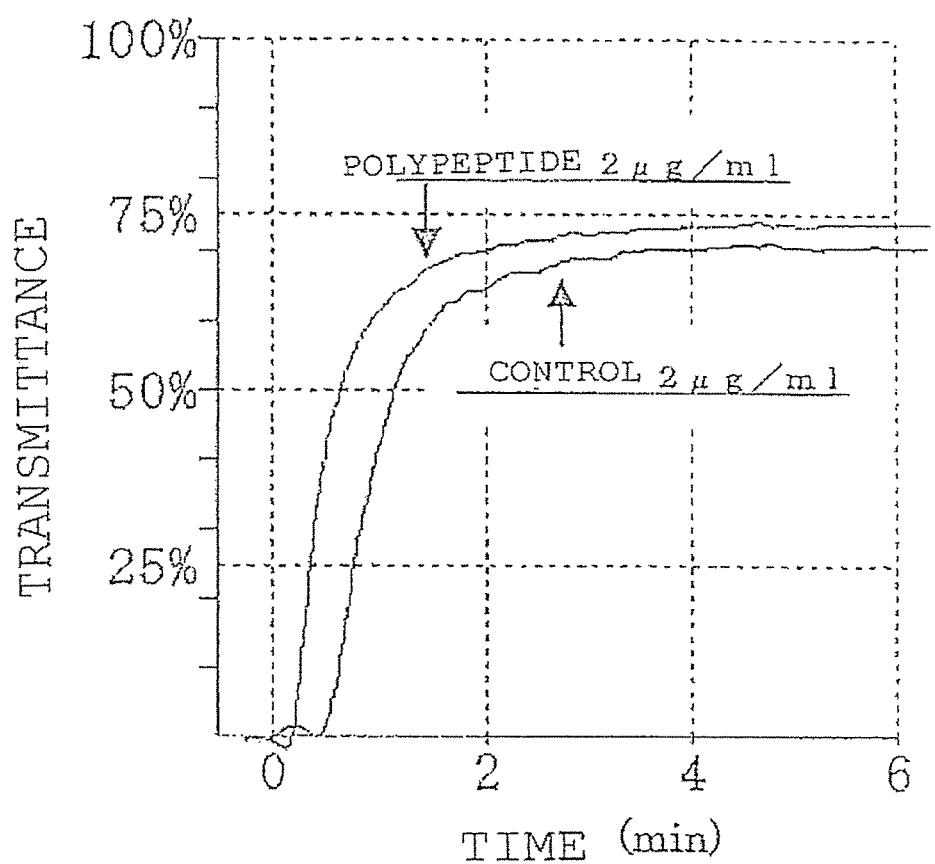
FIG. 1 The figure shows measurement results of aggregation capacity of platelets in Experimental Example 2.

The invention will be described in detail below.
In the invention, amino acid residues are described by the following symbols.

Ala: L-alanine residue
Arg: L-arginine residue
Asn: L-asparagine residue
Asp: L-asparaginic acid residue
Cys: L-cysteine residue
Gln: L-glutamine residue
Glu: L-glutamic acid residue
Gly: glycine residue
His: L-histidine residue
Hyp: L-hydroxyproline residue
Ile: L-isoleucine residue
Leu: L-leucine residue
Lys: L-lysine residue
Met: L-methionine residue
Phe: L-phenylalanine residue
Pro: L-proline residue
Sar: sarcosine residue
Ser: L-serine residue
Thr: L-threonine residue
Trp: L-tryptophan residue
Tyr: L-tyrosine residue
Val: L-valine residue In the specification, the amino acid residues are described with the amino terminal or the N terminal on the left side and the carboxyl terminal or the C terminal on the right side according to the ordinary rule.

The polypeptide as an active ingredient of the invention (which may be referred to as "active ingredient polypeptide") is not particularly limited as far as it is a polypeptide that contains a peptide fragment represented by formula (1) (component A).

$$-(Pro-X-Gly)_n- \quad (1)$$

The repetition number (n) is an integer of from 20 to 5,000, and is preferably an integer of from 20 to 3,000 from the standpoint of platelet aggregation inducing activity and stability of the structure (triple helix structure).

In formula (1), X represents Pro or Hyp. Accordingly, the peptide fragment (component A) includes a case where it contains only a peptide unit represented by formula (2) (component B), a case where it contains only a peptide unit represented by formula (3) (component C), and a case where it contains the peptide unit (component B) and the peptide unit (component C).

$$-(Pro-Pro-Gly)- \quad (2)$$

$$-(Pro-Hyp-Gly)- \quad (3)$$

In the invention, the ratio of the component B and the component C (component B/component C, molar ratio) constituting the peptide fragment (component A) is not particularly limited and is preferably in a range of from 95/5 to 0/100, more preferably in a range of from 50/50 to 0/100, and further preferably in a range of from 10/90 to 0/100, from the standpoint of platelet aggregation inducing activity and stability of the structure (triple helix structure). In the invention, Hyp is 4Hyp (for example, trans-4-hydroxy-L-proline) residue.

The active ingredient polypeptide may contain at least one peptide unit represented by formula (4), may contain at least one peptide unit represented by formula (5), or may contain a peptide fragment containing at least one selected from the peptide unit represented by formula (4) and the peptide unit represented by formula (5).

$$-(Y_1-Y_2-Gly)- \quad (4)$$

$$-(Pro-Z_1-Gly-Z_2-Ala-Gly)- \text{ (SEQ ID NO:13)} \quad (5)$$

In formula (4), $Y_1$ may be an amino acid residue having a carboxyl group (for example, an α-amino acid residue having a carboxyl group or the like), specific examples of which include Asp, Glu and the like, and in the invention, $Y_1$ is Asp or Gly, which may have a carboxyl group at the γ-position. $Y_2$ represents Pro or Hyp.

In formula (5), $Z_1$ represents Gln, Asn, Leu, Ile, Val or Ala, more preferably Gln, Asn, Leu, Val or Ala, and further preferably Gln or Leu. $Z_2$ represents Ile or Leu, and preferably Ile. The peptide unit represented by formula (5) is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12.

The combination of $Z_1$ and $Z_2$ is not particularly limited, and examples thereof include a combination where $Z_1$ is one selected from Gln, Asn, Leu, Ile, Val and Ala (for example, Gln or Leu) and $Z_2$ is Ile so that the peptide unit represented by formula (5) is selected from the group consisting of SEQ ID NO:1, SEQ ID NO:2, SEQ ID NO:3, SEQ ID NO:4, SEQ ID NO:5 and SEQ ID NO:6, and a combination where $Z_1$ is one selected from Gln, Asn, Leu, Ile, Val and Ala (for example, Gln or Leu) and $Z_2$ is Leu so that the peptide unit represented by formula (5) is selected from the group consisting of SEQ ID NO:7, SEQ ID NO:8, SEQ ID NO:9, SEQ ID NO:10, SEQ ID NO:11 and SEQ ID NO:12.

The ratio of the peptide fragment (component A) and at least one selected from the peptide unit represented by formula (4), the peptide unit represented by formula (5), and the peptide fragment containing at least one of the peptide units (component D) (component A/component D, molar ratio) is not particularly limited, and is preferably in a range of from 99/1 to 30/70, more preferably in a range of from 99/1 to 50/50, and further preferably in a range of from 99/1 to 70/30, from the standpoint of platelet aggregation inducing activity and stability of the structure (triple helix structure).

The active ingredient polypeptide may contain an amino acid residue and a peptide residue other than the above in such a range that does not impair the physical and biological properties thereof.

The active ingredient polypeptide may be a salt with an inorganic acid (such as hydrochloric acid, sulfuric acid and the like), an organic acid (such as acetic acid, lactic acid, maleic acid, oxalic acid, citric acid and the like), a metal (such as sodium, potassium and the like), or an organic base (such as trimethylamine, triethylamine and the like). The salt compound of the polypeptide may be used in the invention solely or as a combination of two or more of them.

The active ingredient polypeptide preferably exhibits positive Cotton effect at a wavelength of from 220 to 230 nm and negative Cotton effect at a wavelength of from 195 to 205 nm in a circular dichroic spectrum. The use of the active ingredient polypeptide exhibiting the Cotton effect provides a platelet aggregation inducing substance having practically sufficient activity. The Cotton effect means a phenomenon occurring due to an optically active substance that exhibits a difference between absorption coefficients to clockwise and anticlockwise circularly polarized light at a particular wavelength.

The active ingredient polypeptide may have a triple helix structure. The polypeptide chain forming a triple helix structure may be in a linear form or may have one or more branch. In the case where the polypeptide chain has a branch, the triple helix structure may be formed behind the branch point, or the branch point may be formed behind the triple helix structure.

The molecular weight of the active ingredient polypeptide is not particularly limited, and is preferably in a range of from 10,000 to 500,000,000 from the standpoint of platelet aggregation inducing activity and stability of the structure (triple helix structure).

The particle diameter of the active ingredient polypeptide is not particularly limited, and is preferably in a range of from 0.01 to 1,000 μm, in terms of a diameter measured with a dynamic light scattering particle diameter measuring apparatus or a laser diffraction-scattering particle diameter measuring apparatus, from the standpoint of platelet aggregation inducing activity.

The viscosity of the active ingredient polypeptide is preferably in a range of from 10 to 10,000 mPa·s, in terms of a viscosity measured for a 1 wt % aqueous solution of the polypeptide under a condition of 20° C. with an E-type viscometer, from the standpoint of platelet aggregation inducing activity.

The active ingredient polypeptide may contain only the peptide fragment (component A), and may contain additionally an amino acid residue and an alkylene shown below in such a range that does not impair the advantages of the invention.

Examples of the amino acid residue include at least one amino group selected from Ala, Arg, Asn, Asp, Cys, Gln, Glu, Gly, His, Hyp, Ile, Leu, Lys, Met, Phe, Pro, Sar, Ser, Thr, Trp, Tyr, Val, or a peptide residue containing several of them bonded to each other.

The alkylene may be linear or branched and is not particularly limited, and examples thereof include an alkylene having from 1 to 18 carbon atoms, and practically an alkylene having from 2 to 12 carbon atoms.

The platelet aggregation inducing substance of the invention may contain a substance other than the active ingredient polypeptide in such a range that does not impair the advantages of the invention. The substance may be selected in consideration of preservability, handleability, stability of activity and the like and is not particularly limited, and examples thereof include preservation solvents described later.

A method for producing the active ingredient polypeptide will be described in detail below.

The active ingredient polypeptide may be obtained in any method. However, when a peptide fragment is condensed in a solvent, polymerization proceeds to provide the active ingredient polypeptide without repeated deprotection and formation of amino acid bond, and therefore such a method is preferably employed that a peptide fragment containing amino acids constituting the active ingredient polypeptide is subjected to condensation reaction in a solvent.

The peptide fragment referred in the invention is a peptide fragment containing from 3 to 90 residues. Examples of the peptide fragment that can be used for producing the active ingredient polypeptide include peptide fragments shown below.

No. 1-No. 18
wherein o represents an integer of from 1 to 10.
No. 19-No. 67
wherein p represents an integer of from 1 to 10, and q represents an integer of from 1 to 10.

Among these, the peptide fragment No. 1 or No. 2 is necessarily used for producing the active ingredient polypeptide. The peptide fragments Nos. 3 to 67 may be used appropriately. Other peptide fragments than the above may be used in such a range that does not impair the advantages of the invention.

The peptide fragment No. 1 or No. 2 and the peptide fragments Nos. 3 to 67 or a peptide fragment containing these peptide fragments and other peptide fragments than these may be used for producing the active ingredient polypeptide.

The integers o, p and q in the aforementioned peptide fragments and the ratios of the peptide fragments used in the condensation reaction are not particularly limited and are determined based on the ratio of the component B and the component C and the ratio of the component A and the component D of the intended active ingredient polypeptide.

In view of facility of the condensation reaction and availability of the peptide fragments, o, p and q are preferably each independently an integer of from 1 to 10, more preferably an integer of from 1 to 5, and particularly preferably 1.

The peptide fragments Nos. 1 to 67 can be obtained by a known solid phase synthesis method or liquid phase synthesis method.

The condensation reaction of the peptide fragments is generally performed in a solvent. The solvent may be one capable of dissolving (partly or wholly dissolving) or suspending the peptide fragments as raw materials, and water and an organic solvent can be generally used. Specific examples thereof include water, an amide compound (such as dimethylformamide, dimethylacetamide, hexamethylphosphoramide and the like), a sulfoxide compound (such as dimethylsulfoxide and the like), a nitrogen-containing cyclic compound (such as N-methylpyrrolidone, pyridine and the like), a nitrile compound (such as acetonitrile and the like, an ether compound (such as dioxane, tetrahydrofuran and the like), an alcohol compound (such as methyl alcohol, ethyl alcohol, propyl alcohol and the like), and mixed solvents thereof. Among the solvents, water, dimethylformamide and dimethylsulfoxide are preferably used.

The reaction of the peptide fragments is preferably performed in the presence of a dehydrating agent (dehydration condensing agent). Upon reacting in the presence of a dehydration condensing agent and a condensation assistant, the condensation reaction smoothly proceeds while suppressing dimerization and cyclization from occurring.

The dehydration condensing agent is not particularly limited as far as it effectively performs dehydration condensation in the solvent, and examples thereof include a carbodiimide condensing agent (such as diisopropylcarbodiimide (DIPC), 1-ethyl-3-(3-dimethylaminopropyl)carbodiimide (EDC=WSCI), 1-ethyl-3-(3-dimethylaminopropyl)carbodiimide hydrochloride (WSCI.HCl), dicyclohexylcarbodiimide (DCC) and the like), a fluorophosphate condensing agent (such as O-(7-azabenzotriazol-1-yl)-1,1,3,3-tetramethyluronium hexafluorophosphate, O-benzotriazol-1-yl-N,N,N',N'-tetramethyluronium hexafluorophosphate, benzotriazol-1-yl-oxy-tris-pyrrolidinophosphonium hexafluorophosphate, benzotriazol-1-yl-tris(dimethylamino)phosphonium hexafluorophosphide (BOP) and the like), and diphenylphosphorylazide (DPPA).

The dehydration condensing agents may be used solely or as a mixture by combining two or more of them. Preferred examples of the dehydration condensing agent include a carbodiimide condensing agent (such as 1-ethyl-3-(3-dimethylaminopropyl)carbodiimide and 1-ethyl-3-(3-dimethylaminopropyl)carbodiimide hydrochloride).

The condensation assistant is not particularly limited as far as it accelerates the condensation reaction, and examples thereof include an N-hydroxy polyhydric carboxylic imide compound (such as an N-hydroxydicarboxylic imide compound, e.g., N-hydroxysuccinimide (HONSu), N-hydroxy-5-norbornene-2,3-dicarboxylic imide (HONB) and the like), an N-hydroxytriazole compound (such as an N-hydroxybenzotriazole compound, e.g., 1-hydroxybenzotriazole (HOBt) and the like), a triazine compound, such as 3-hydroxy-4-oxo-3,4-dihydro-1,2,3-benzotriazine (HOOBt) and the like, and ethyl 2-hydroxyimino-2-cyanoacetate.

The condensation assistants may be used solely or as a mixture by combining two or more of them. Preferred examples of the condensation assistant include an N-hydroxydicarboxylic imide compound (such as HONSu and the like), and an N-hydroxybenzotriazole or N-hydroxybenzotriazine compound (such as HOBt and the like).

The dehydration condensing agent and the condensation assistant are preferably used by suitably combining. Examples of the combination of the dehydration condensing agent and the condensation assistant include DCC-HONSu (HOBt or HOOBt) and WSCI-HONSu (HOBt or HOOBt).

The amount of the dehydration condensing agent used is generally in a range of from 0.7 to 5 mol, preferably from 0.8 to 2.5 mol, and further preferably from 0.9 to 2.3 mol (e.g., 1 to 2 mol), per 1 mol in total of the peptide fragments in the case where a nonaqueous solvent containing no water is used. In a solvent containing water (aqueous solvent), in consideration of deactivation of the dehydration condensing agent with water, the amount of the dehydration condensing agent used is generally in a range of from 2 to 500 mol, preferably from 5 to 250 mol, and further preferably from 10 to 125 mol, per 1 mol in total of the peptide fragments.

The amount of the condensation assistant used is generally in a range of from 0.5 to 5 mol, preferably from 0.7 to 2 mol, and further preferably from 0.8 to 1.5 mol, irrespective of the kind of the solvent.

In the condensation reaction, the pH of the reaction system may be controlled, and a base that does not participate the reaction may be added. The pH can be controlled generally with an inorganic base (such as sodium hydroxide, potassium hydroxide, sodium carbonate, sodium hydrogencarbonate and the like), an organic base, an inorganic acid (such as hydrochloric acid and the like), or an organic acid, and the pH of the reaction solution is generally controlled around neutral (pH of about from 6 to 8). Examples of the base that does not participate the condensation reaction include a tertiary amine compound, for example, a trialkylamine compound, such as trimethylamine, triethylamine, diisopropylethylamine and the like, a heterocyclic tertiary amine compound, such as N-methylmorpholine, pyridine and the like, and the like. The amount of the base used is generally selected from a range of from 1 to 2 times the total molar number of the peptide fragments.

In the polypeptide thus obtained, the reagents used in the reaction remain. These affect the platelet aggregation inducing activity of the active ingredient polypeptide and the function of platelets themselves, and therefore the reagents remaining are preferably removed by a known method, such as a dialysis method, a column method, an ultrafiltration method and the like. In consideration of stability and handling facility of the polypeptide, it is preferred that the reaction solvent is replaced with a preservation solvent. The reaction solvent can be replaced with the target preservation solvent by using the target preservation solvent as a dialysis external fluid in the dialysis method, or by using the target preservation solvent as a mobile phase in the column method.

The preservation solvent is not particularly limited as far as it can suppress alterations of the physical properties and biological properties of the resulting active ingredient polypeptide. Examples thereof include water, physiological saline and a buffer having a buffering function in a range of from weak acid to weak alkali. It is preferred that such a substance is not contained that affects the function of platelets themselves and the blood coagulation factors. Examples of the substance that affects the function of platelets themselves include a chelating agent that chelates calcium ions in the blood plasma, such as ethylenediaminetetraacetic acid, sodium citrate and the like, an antiplatelet agent that depresses the function of platelets, and a substance that activates platelets. Examples of the substance that affects the blood coagulation factors include a substance containing calcium ions, which accelerate coagulation of blood or platelet-rich plasma having been subjected to anticoagulation treatment.

The active ingredient polypeptide has platelet aggregation inducing activity. Accordingly, the platelet aggregation inducing substance of the invention containing the same can be used for evaluation of aggregation capacity of platelets. The method for measuring aggregation capacity of platelets is not particularly limited as far as it is a method using an inducing substance. Examples of the usable methods include an absorbance method (transmitted light method) where the extent of aggregation of platelets is determined by absorbance (transmittance), an impedance method where it is determined by change of electric resistance between platinum electrodes, a particle counting method where the extent of aggregation of platelets is estimated from the number of single platelets that do not participate aggregation of platelets by using a particle measuring equipment, a light scattering method using scattered light, a micromesh filter method using a filter, and the like.

The transmitted light method is being commonly employed clinically. The transmitted light method employs the following principle. Platelet-rich plasma (which may be hereinafter referred to as "PRP") is obtained by centrifugation, and then platelet-poor plasma (which may be hereinafter referred to as "PPP") is obtained by centrifugation. The number of platelets in the PRP is controlled to from 200,000 to 400,000 $\mu L^{-1}$, and a prescribed amount (from 200 to 500 µL) of the PRP and the PPP are placed in a cuvet and heated to 37° C., to which the inducing substance is added under stirring with a magnetic stirrer. Thereafter, the transmittance of the PRP increased associated with aggregation is measured by a spectrophotometer with the PPP as a control. As evaluation of aggregation of platelets, the maximum value of the change rate of the transmittance, the maximum change rate of the platelet aggregation curve, and the like are used, and such a method may be used that uses two or three kinds of concentrations from low concentration to high concentration. In general, a test using two concentrations is being frequently employed, and commercially available collagen has a low concentration of from 0.2 to 1 µg/mL (final concentration) or a high concentration of from 2 to 4 µg/mL (final concentration).

In the case where the platelet aggregation inducing substance of the invention is applied to the transmitted light method, the aforementioned operation may be used except for adjustment of the concentration. In the case where the concentration of the platelet aggregation inducing substance of the invention is adjusted, a diluent may be arbitrarily selected from water, physiological saline and a buffer having the same composition as the preservation fluid, and is preferably water or physiological saline. A solution diluted with water at a final concentration of 0.05 µg/mL has an inducing capability of aggregation of platelets that is equivalent to commercially available collagen (produced by MC Medical, Inc.) at 2 µg/mL.

The platelet aggregation inducing substance of the invention has sufficiently high platelet aggregation inducing activity as compared to commercially available collagen, and has no necessity of crosslinking. The active ingredient polypeptide used in the invention is non-crosslinked, and thus there is no influence on the function of platelets themselves due to a remaining crosslinking agent, whereby the aggregation capacity of platelets can be precisely evaluated. Furthermore, the process can be largely reduced owing to the absence of crosslinking.

The platelet aggregation inducing substance of the invention has adhesion capability to platelets and thus can be used for evaluation of adhesion capability of platelets, a verification test of adhesion of platelets to collagen under flowing, and the like. As a method for measuring the aggregation capacity of platelets, a Baumgartner method, a method using a glass bead tube with negative charge, and the like have been known, and the method is not limited as far as the method does not use an intravascular subcutaneous tissue, examples of which include a collagen-coated glass bead method with glass beads or the like coated with collagen, and the like. Examples of the method for verifying adhesion of platelets to collagen under flowing include a flow chamber method using a chamber of glass or the like coated with collagen inside, the use thereof by coating on an inner surface of a capillary tube or the like, and the like. A method for immobilizing collagen to beads or the like may be arbitrarily selected from a method for immobilizing with covalent bond and a method for immobilizing without covalent bond.

EXAMPLE

The invention will be described in more detail with reference to examples below. However, the invention is not limited to the examples.

Experimental Example 1

Synthesis of Polypeptide 1 g of a peptide fragment represented by Pro-Hyp-Gly synthesized by a liquid phase method was dissolved in 20 mL of a 10 mM phosphate buffer (pH 7.4), and cooled to 4° C. 473 mg of 1-hydroxybenzotriazole and 3.35 g of 1-ethyl-3-(3-dimethylaminopropyl)carbodiimide hydrochloride at 4° C. were added thereto, followed by stirring at 4° C. for 2 hours and then stirring for 46 hours after heating to 20° C. After completing the reaction, the reaction solution was diluted twice with extra-pure water, and the resulting solution was placed in a cellulose tube for dialysis (UC27-32-100, produced by Viscase Corporation) and was dialyzed against 2 L of pure water for 48 hours. The pure water was exchanged four times with an interval of 6 hours or more.

After dialyzing, the solution was diluted 50 times (volume ratio) with water and subjected to gel permeation chromatography (high performance liquid chromatography: 1100 Series produced by Agilent Technologies, column: OHpak SB-806m HQ produced by Shodex, flow rate: 1.0 mL/min, mobile phase: 20 mM potassium phosphate buffer (pH 3.0)/methanol=8/2 (volume ratio)), and thus a peak of a polypeptide was observed in a range of molecular weight of from 10,000 to 500,000,000.

Separately, the solution after dialyzing was diluted 60 times (volume ratio) with water and measured for circular dichroic spectrum (circular dichroic polarimeter J-820, produced by Jasco Corporation, light path length: 1 mm), whereby positive Cotton effect was observed at 225 nm, and negative Cotton effect was observed at 198 nm.

Experimental Example 2

4.5 mL of blood was collected from a subject A with a vacuum blood collection tube containing 0.5 mL of 3.8 wt % by weight sodium citrate, and was well mixed to attain anticoagulation treatment. Subsequently, the blood having been subjected to anticoagulation treatment was subjected to centrifugation at 100 g for 15 minutes, and a supernatant was collected as PRP. Centrifugation was further performed at 2,000 g for 15 minutes, and a supernatant was collected as PPP. The aggregation capacity was evaluated in such a manner that the time course of the transmittance after adding the polypeptide solution prepared in Experimental Example 1 was recorded by using a platelet aggregation measuring apparatus, Easy TRACER ET-800 (produced by Tokyo Koden Co., Ltd.), with the transmittance of the PRP before adding an aggregation inducing substance being designated as 0% and the transmittance of the PPP being designated as 100%. The polypeptide solution was added to make a final concentration of the polypeptide of 2 μg/mL, and the time course of the transmittance was recorded. A commercially available aggregation inducing substance of collagen (MC Medical, Inc.) as a control was added to make a final concentration of collagen of 2 μg/mL, and the time course of the transmittance was recorded. The results are shown in FIG. 1.

Experimental Example 3

Figure 2:
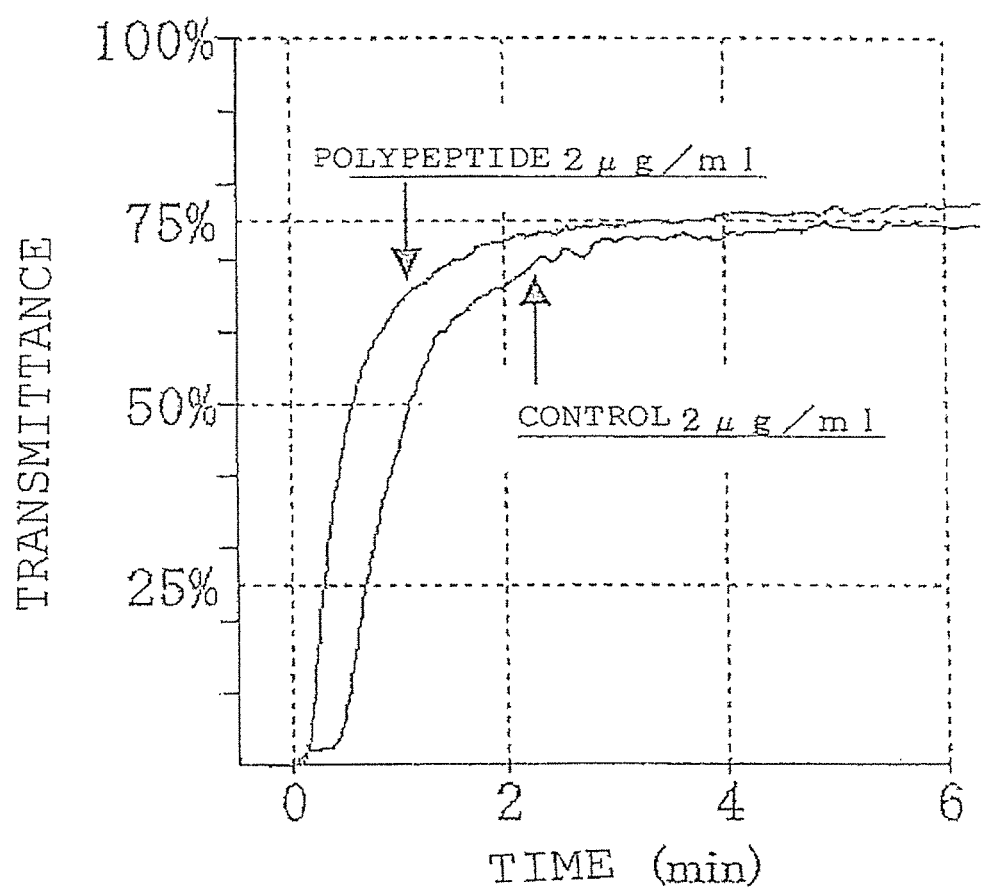
FIG. 2 The figure shows measurement results of aggregation capacity of platelets in Experimental Example 3.

The aggregation capacity of platelets was evaluated according to the method disclosed in Experimental Example 2 except that 4.5 mL of blood collected from a subject B was used. The results are shown in FIG. 2.

Experimental Example 4

Figure 3:
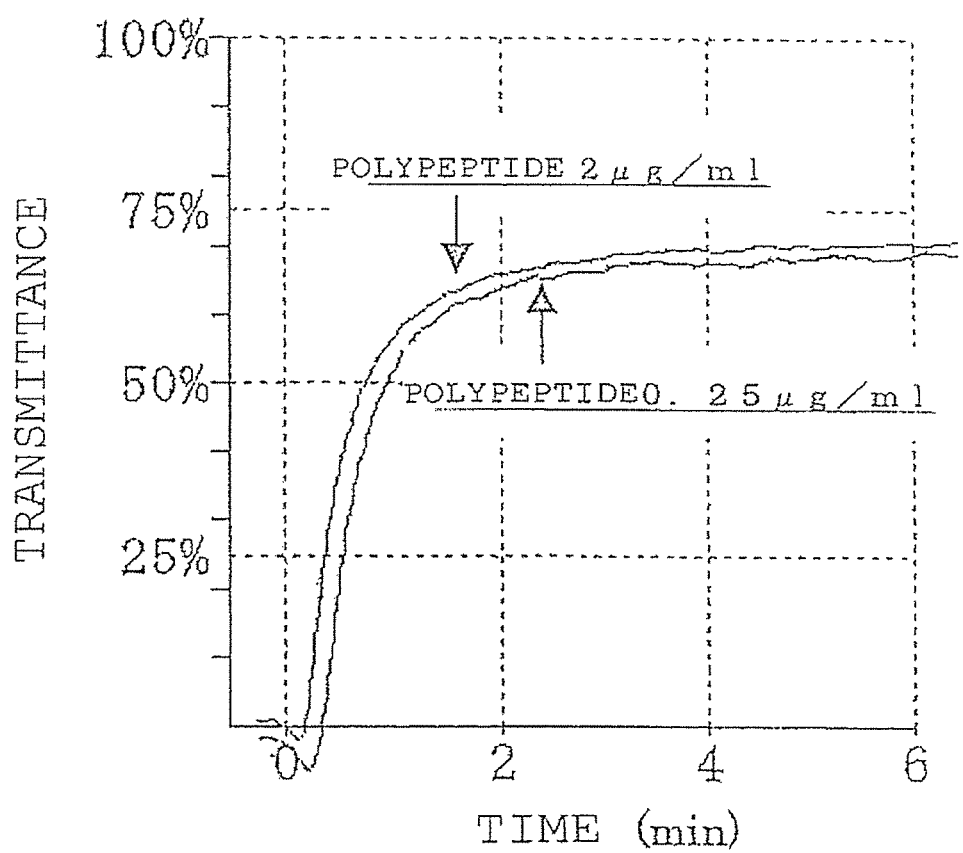
FIG. 3 The figure shows measurement results of aggregation capacity of platelets in Experimental Example 4.
Figure 4:
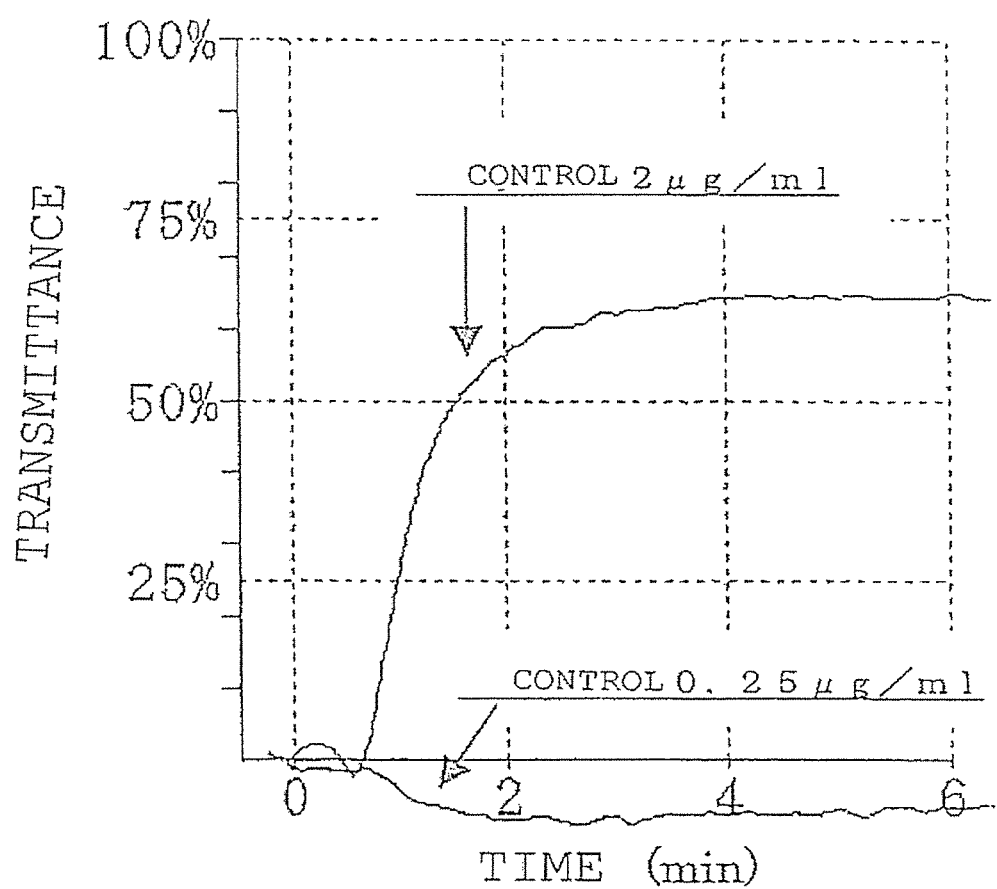
FIG. 4 The figure shows measurement results of aggregation capacity of platelets in Experimental Example 4.

The aggregation capacity of platelets was evaluated according to the method disclosed in Experimental Example 2 except that 4.5 mL of blood collected from a subject C was used, the final concentration of the polypeptide was 2.0 μg/mL or 0.25 μg/mL, and the final concentration of collagen for comparison was 2.0 μg/mL or 0.25 μg/mL. The results are shown in FIGS. 3 and 4.

Experimental Example 5

Figure 5:
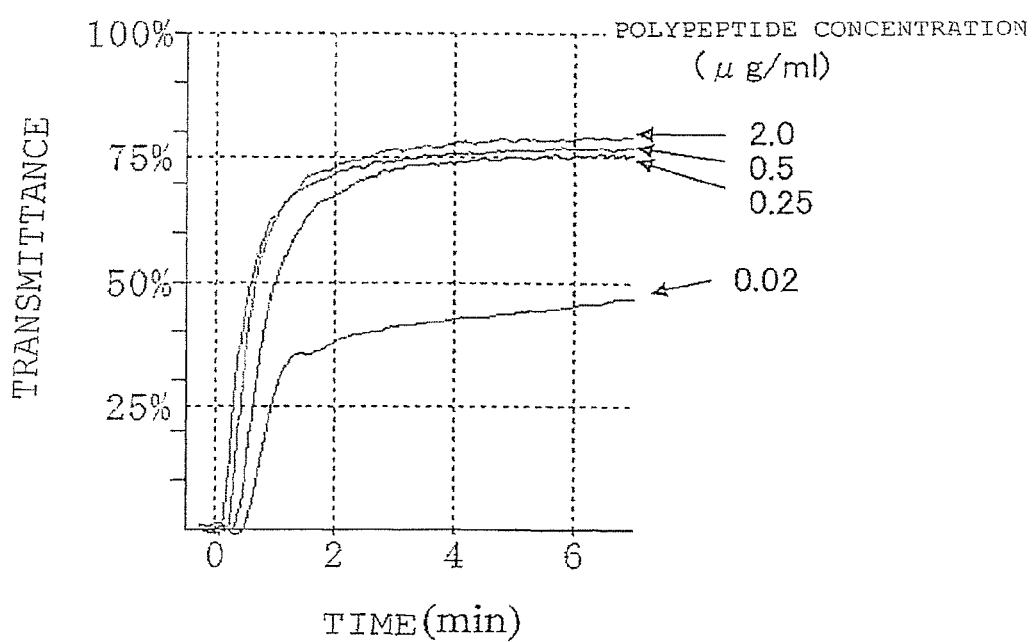
FIG. 5 The figure shows measurement results of aggregation capacity of platelets in Experimental Example 5.
Figure 6:
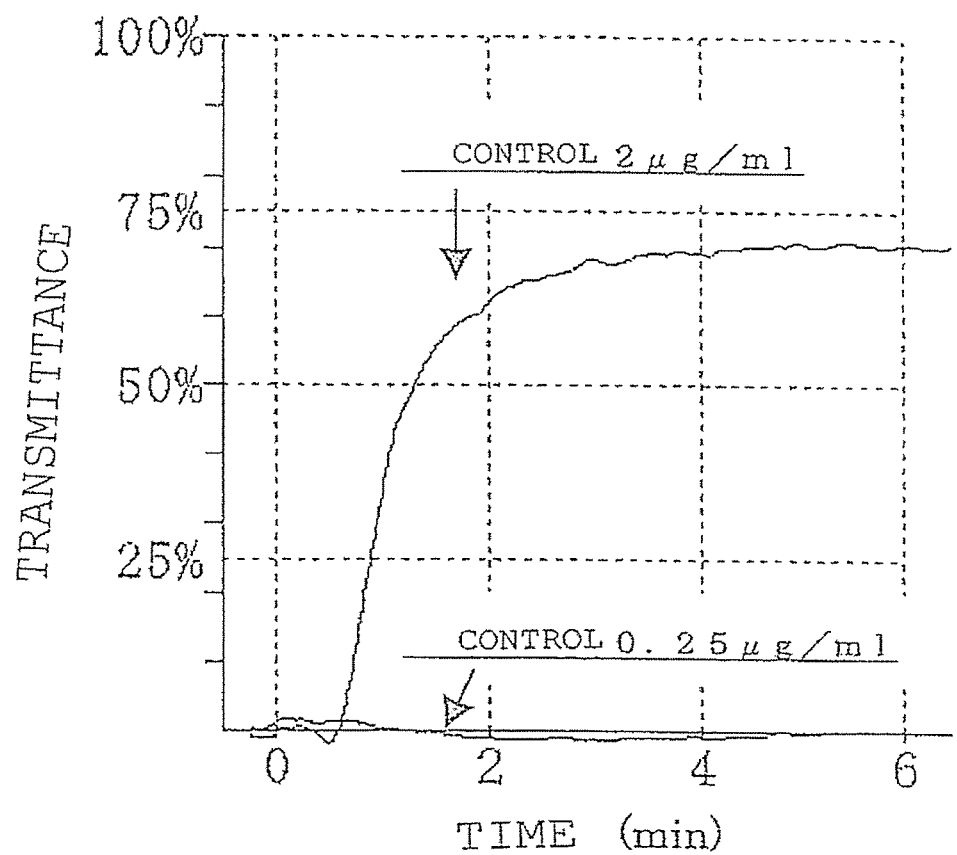
FIG. 6 The figure shows measurement results of aggregation capacity of platelets in Experimental Example 5.

The aggregation capacity of platelets was evaluated according to the method disclosed in Experimental Example 2 except that 4.5 mL of blood collected from a subject D was used, the final concentration of the polypeptide was 2.0 μg/mL, 0.25 μg/mL, 0.05 μg/mL or 0.02 μg/mL, and the final concentration of collagen for comparison was 2.0 μg/mL or 0.25 μg/mL. The results are shown in FIGS. 5 and 6.

Experimental Example 6

Figure 7:
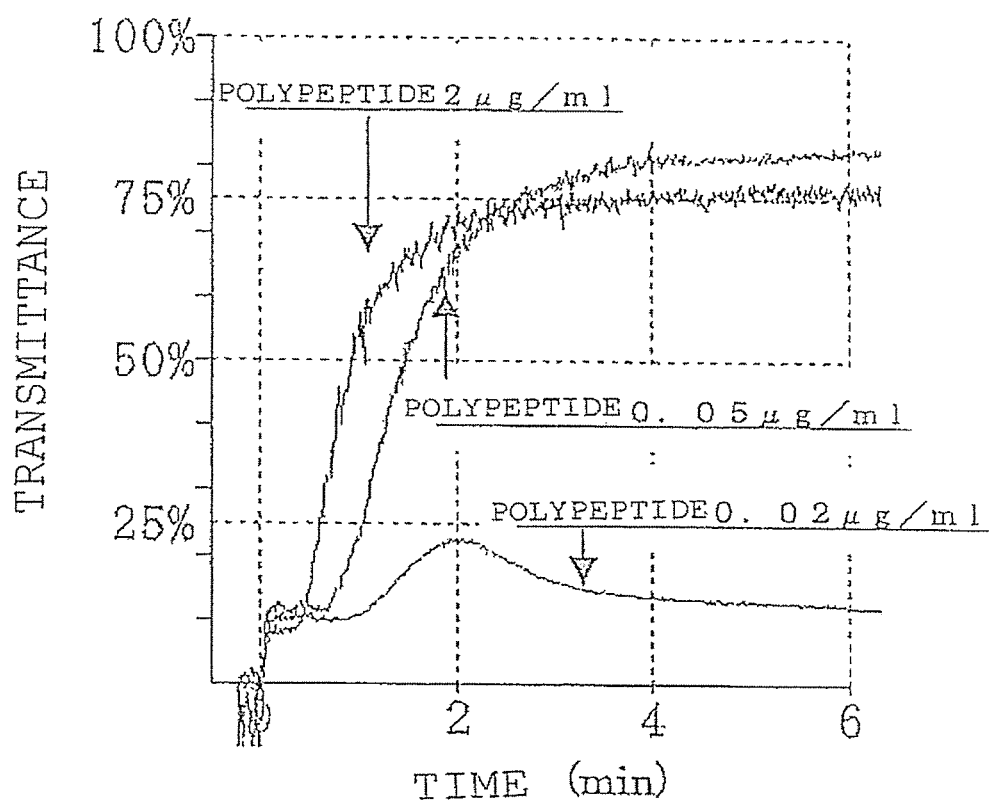
FIG. 7 The figure shows measurement results of aggregation capacity of platelets in Experimental Example 6.
Figure 8:
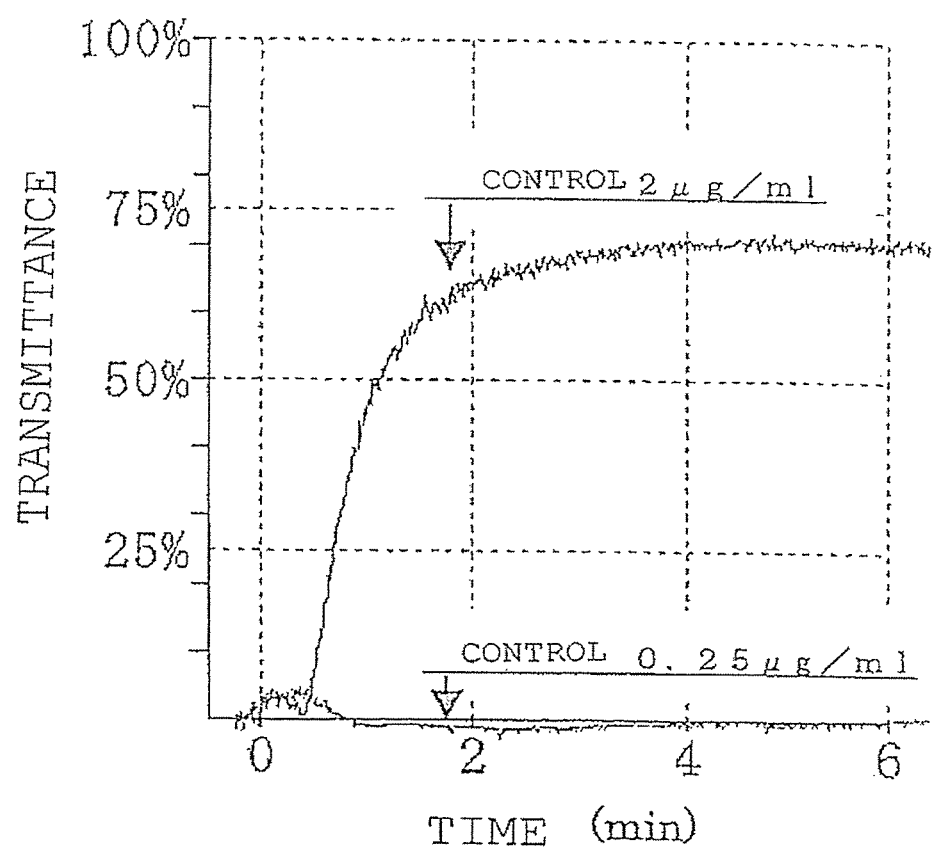
FIG. 8 The figure shows measurement results of aggregation capacity of platelets in Experimental Example 6.

The aggregation capacity of platelets was evaluated according to the method disclosed in Experimental Example 2 except that 13.5 mL of blood collected from a subject A was used, the final concentration of the polypeptide was 0.05 μg/mL, 0.025 μg/mL or 0.015 μg/mL, and the final concentration of collagen for comparison was 2.0 μg/mL or 0.25 μg/mL. The results are shown in FIGS. 7 and 8.

Experimental Example 7

Measurement of Aggregation of Platelets in the Presence or Absence of Aspirin (1) Synthesis of Polypeptide 1 g of a peptide fragment represented by Pro-Hyp-Gly synthesized by a liquid phase method was dissolved in 20 mL of a 10 mM phosphate buffer (pH 7.4), and cooled to 4° C. 473 mg of 1-hydroxybenzotriazole and 3.35 g of 1-ethyl-3-(3-dimethylaminopropyl)carbodiimide hydrochloride at 4° C. were added thereto, followed by stirring at 4° C. for 2 hours and then stirring for 46 hours after heating to 20° C. After completing the reaction, the reaction solution was placed in a cellulose tube for dialysis (UC27-32-100, produced by Viscase Corporation) and was dialyzed against 2 L of pure water for 48 hours. The pure water was exchanged four times with an interval of 6 hours or more.

After dialyzing, the solution was diluted 100 times (volume ratio) with physiological saline. The 100-time diluted solution was filtered (0.2 μm, cellulose acetate membrane, 25CS020AS, available from Advantec Toyo Co., Ltd.) and then further diluted 50 times (volume ratio) with physiological saline. After diluting 50 times, the concentration of the polypeptide in the solution measured by an absorbance method (wavelength: 215 nm) was 0.29 μg/mL.

(2) Measurement of Aggregation of Platelets

PRP that was treated with aspirin (aspirin-treated PRP) and PRP that was not treated with aspirin (aspirin-non-treated PRP) were used for measuring aggregation of platelets. PRP used was PRP obtained in Experimental Example 2, to which 1/10 amount (volume ratio) of a 10 mM aspirin solution, which was obtained by diluting aspirin (acetylsalicylic acid, produced by Wako Pure Chemical Industries, Ltd., special grade reagent) with physiological saline, was added, followed by heating to 37° C. for 30 minutes, to provide the aspirin-treated PRP. 1/10 amount (volume ratio) of physiological saline was added to PRP obtained in Experimental Example 2, followed by heating to 37° C. for 30 minutes, to provide the aspirin-non-treated PRP.

The aggregation capacity was evaluated in such a manner that the time course of the transmittance after adding the polypeptide solution prepared in this Experimental Example was recorded by using a platelet aggregation measuring apparatus, Easy TRACER ET-800 (produced by Tokyo Koden Co., Ltd.), with the transmittance of the PRP before adding an aggregation inducing substance being designated as 0% and the transmittance of the PPP being designated as 100%.

Figure 9:
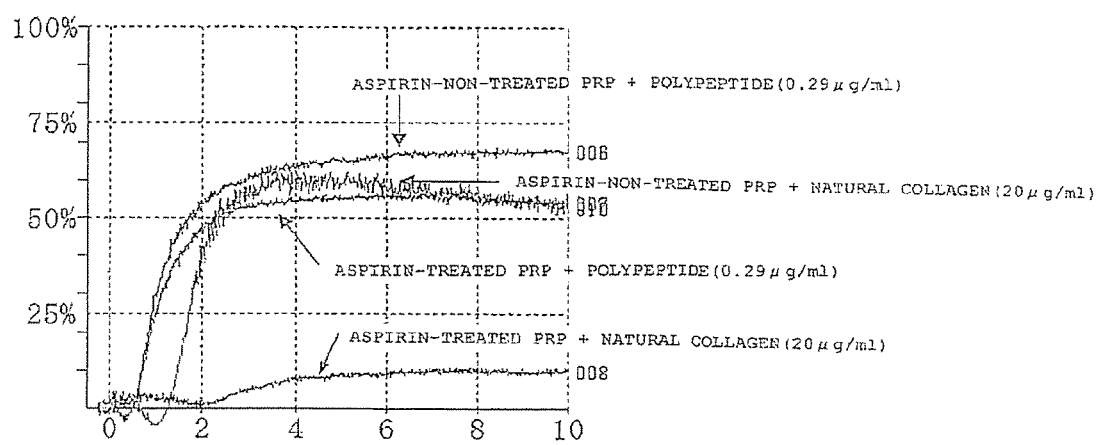
FIG. 9 The figure shows measurement results of aggregation capacity of platelets in Experimental Example 7.

22 μL of the polypeptide solution (polypeptide concentration: 0.29 μg/mL) was added to each of 200 μL of the aspirin-treated PRP and 200 μL of the aspirin-non-treated PRP, and the time course of the transmittance was recorded. Subsequently, natural collagen, Collagen Reagent "Horm" (1 mg/mL), available from Moriya Sangyo Co., Ltd., was diluted 10 times (volume ratio) with the accompanying diluent and was further diluted 5 times (volume ratio) with physiological saline to provide a solution (collagen concentration: 20 μg/mL), which was added to each of 200 μL of the aspirin-treated PRP and 200 μL of the aspirin-non-treated PRP, and the time course of the transmittance was recorded. The results are shown in FIG. 9.

In the case where natural collagen was used as an aggregation inducing substance, no aggregation of platelets was observed for the aspirin-treated PRP although aggregation of platelets was found for the aspirin-non-treated PRP. In the case where the polypeptide of this Experimental Example was used, on the other hand, aggregation of platelets was observed for both the aspirin-treated PRP and the aspirin-non-treated PRP even with the concentration thereof of about 1/70 of the natural collagen.

INDUSTRIAL APPLICABILITY

The thrombin variant of the invention is significantly lowered in affinity to a heparin-like substance (heparan sulfate), thrombomodulin and/or integrin, which are present on the blood vessel wall, and has high antithrombotic capacity, and thus it can be effectively used as remedy for thrombotic disease and the like without side effect.

The invention claimed is:

1. A platelet aggregation inducing substance comprising as an active ingredient an un-crosslinked polypeptide having a peptide fragment represented by formula (1) (component A):

$$-(Pro-X-Gly)_n- \quad (1)$$

wherein n represents an integer of from 20 to 5,000,
wherein the peptide fragment of formula (1) is selected from the group consisting of -(Pro-Pro-Gly)- (Component B) and -(Pro-Hyp-Gly)- (Component C), wherein the molar ratio of the Component B:Component C in said peptide fragment is 10/90 to 0/100, and
wherein said un-crosslinked polypeptide is capable of inducing said platelet aggregation even in the presence of an inhibitory amount of aspirin, as compared to collagen.

2. The platelet aggregation inducing substance according to claim 1, wherein the polypeptide further comprises, as a component D, at least one selected from the group consisting of a peptide unit represented by formula (4), a peptide unit represented by formula (5) and a peptide fragment containing at least one of the peptide units:

$$-(Y_1-Y_2-Gly)- \quad (4)$$

$$-(Pro-Z_1-Gly-Z_2-Ala-Gly)- \text{ (SEQ ID NO:13)} \quad (5)$$

wherein $Y_1$ represents Asp or Glu, which may have a carboxyl group at the γ-position; $Y_2$ represents Pro or Hyp; $Z_1$ represents Gln, Asn, Leu, Ile, Val or Ala; $Z_2$ represents Ile or Leu, and the peptide unit represented by formula (5) is selected from the group consisting of SEQ ID NO:1, SEQ ID NO:2, SEQ ID NO:3, SEQ ID NO:4, SEQ ID NO:5, SEQ ID NO: 6, SEQ ID NO:7, SEQ ID NO:8, SEQ ID NO:9, SEQ ID NO:10, SEQ ID NO:11 and SEQ ID NO:12.

3. The platelet aggregation inducing substance according to claim 2, wherein a ratio of the peptide fragment (component A) to the component D is in a range of from 99/1 to 30/70.

4. The platelet aggregation inducing substance according to claim 1, wherein the polypeptide exhibits positive Cotton effect at a wavelength of from 220 to 230 nm and negative Cotton effect at a wavelength of from 195 to 205 nm in a circular dichroic spectrum.

5. The platelet aggregation inducing substance according to claim 1, wherein the polypeptide has a molecular weight in a range of from 10,000 to 500,000,000.

6. The platelet aggregation inducing substance according to claim 1, wherein the polypeptide has a particle diameter in a range of from 0.01 to 1,000 μm.

7. The platelet aggregation inducing substance according to claim 1, wherein the polypeptide has a viscosity in a range of from 10 to 10,000 mPa·s, wherein the viscosity is measured for a 1 wt % aqueous solution of the polypeptide under a condition of 20° C. with an E-type viscometer.

8. The platelet aggregation inducing substance according to claim 1, wherein the polypeptide further comprises, as a component D, at least one selected from the group consisting of a peptide unit represented by formula (4), a peptide unit represented by formula (5) and a peptide fragment containing at least one of the peptide units:

$$-(Y_1-Y_2-Gly)- \quad (4)$$

$$-(Pro-Z_1-Gly-Z_2-Ala-Gly)- \quad (5)$$

wherein $Y_1$ represents Asp or Glu, which may have a carboxyl group at the γ-position; $Y_2$ represents Pro or Hyp; $Z_1$ represents Gln, Asn, Leu, Ile, Val or Ala; and $Z_2$ represents Ile or Leu.

9. The platelet aggregation inducing substance according to claim 8, wherein a ratio of the peptide fragment (component A) to the component D is in a range of from 99/1 to 30/70.

* * * * *

```
                        SEQUENCE LISTING

<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Synthetic Construct

<400> SEQUENCE: 1

Pro Gln Gly Ile Ala Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic Construct

<400> SEQUENCE: 2

Pro Asn Gly Ile Ala Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct

<400> SEQUENCE: 3

Pro Leu Gly Ile Ala Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Pro Ile Gly Ile Ala Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Construct

<400> SEQUENCE: 5

Pro Val Gly Ile Ala Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Construct

<400> SEQUENCE: 6
```

Pro Ala Gly Ile Ala Gly
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic Construct

<400> SEQUENCE: 7

Pro Gln Gly Leu Ala Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Pro Asn Gly Leu Ala Gly
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Construct

<400> SEQUENCE: 9

Pro Leu Gly Leu Ala Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

Pro Ile Gly Leu Ala Gly
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Pro Val Gly Leu Ala Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

```
Pro Ala Gly Leu Ala Gly
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is  Gln, Asn, Leu, Ile, Val or Ala.
<220> FEATURE:
<221> NAME/KEY: MISC_FEATURE
<222> LOCATION: (4)..(4)
<223> OTHER INFORMATION: Xaa is  Ile or Leu.

<400> SEQUENCE: 13

Pro Xaa Gly Xaa Ala Gly
1               5
```